United States Patent
Sharma

(12) 
(10) Patent No.: US 8,632,754 B2
(45) Date of Patent: *Jan. 21, 2014

(54) TOOTH SENSITIVITY TREATMENT COMPOSITIONS

(75) Inventor: Deepak Sharma, Flemington, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 782 days.

This patent is subject to a terminal disclaimer.

(21) Appl. No.: 12/534,621

(22) Filed: Aug. 3, 2009

(65) Prior Publication Data

US 2011/0027196 A1    Feb. 3, 2011

(51) Int. Cl.
*A61Q 11/00* (2006.01)
*A61K 8/00* (2006.01)
*A61K 8/29* (2006.01)

(52) U.S. Cl.
USPC .............................................. 424/49; 424/55

(58) Field of Classification Search
USPC ............................ 424/49, 55; 433/216, 217.1
See application file for complete search history.

(56) References Cited

U.S. PATENT DOCUMENTS

| | | | |
|---|---|---|---|
| 3,699,137 A | | 10/1972 | Termin et al. |
| 4,289,754 A | * | 9/1981 | Dhabhar et al. ................. 424/52 |
| 4,588,756 A | | 5/1986 | Bowen |
| 4,659,751 A | | 4/1987 | Bowen |
| 4,957,568 A | * | 9/1990 | Endres et al. ................. 148/254 |
| 5,211,559 A | * | 5/1993 | Hart et al. ........................ 433/80 |
| 5,352,439 A | * | 10/1994 | Norfleet et al. ................. 424/52 |
| 5,421,550 A | | 6/1995 | Palmer |
| 5,866,631 A | | 2/1999 | Nakagawa et al. |
| 6,083,309 A | | 7/2000 | Tomlinson |
| 2003/0124067 A1 | * | 7/2003 | Yue et al. ......................... 424/52 |
| 2003/0165442 A1 | * | 9/2003 | Baig et al. ........................ 424/57 |
| 2004/0057908 A1 | * | 3/2004 | Bowen et al. .................... 424/49 |
| 2004/0086467 A1 | * | 5/2004 | Curro ............................... 424/52 |
| 2007/0025928 A1 | * | 2/2007 | Glandorf et al. ................ 424/49 |

\* cited by examiner

*Primary Examiner* — Lezah Roberts

(57) ABSTRACT

A tooth sensitivity treatment composition is disclosed. The composition includes a compound of formula I $$M^1\text{-}A\text{-}M^2\text{-}B\text{-}M^1 \qquad (I)$$

wherein: $M^1$ is a monovalent or divalent metal; $M^2$ is a polyvalent metal or metal oxide; and A and B are, independently, selected from the group consisting of $C_2$-$C_6$ diacids, triacids, and tetraacids. Methods for treating tooth sensitivity are also disclosed.

18 Claims, 4 Drawing Sheets

7 treatments 14 treatments 21 treatments 28 treatments 7 treaments 14 treatments 21 treatments 28 treatments Etched dentin prior to treatment with Formulation E Etched dentin after 28 treatments with Formulation E Etched dentin treated with Formulation B for 28 treatments after 2 minutes of sonication Etched dentin treated with Formulation D for 28 treatments after 2 minutes of sonication

TOOTH SENSITIVITY TREATMENT COMPOSITIONS

FIELD OF THE INVENTION

The present invention relates to tooth sensitivity treatment compositions, which have an affinity for dentin and effectively occlude open dentinal tubules.

BACKGROUND OF THE INVENTION

Many people suffer from sensitive teeth, and this condition is often referred as dentinal hypersensitivity, which is a common problem in adult population. It is defined as a transient pain arising from exposed dentin, typically in response to chemical, thermal, tactile or osmotic stimuli that cannot be explained by any other dental defect or pathology. Erosion of the outer surface (enamel) of the tooth and/or gum recession often results in exposure of dentinal tubules providing pathways between oral cavity and nerve fibers in the pulp. It has been shown in-vivo that a pressure gradient exists across dentin, which causes outward flow of fluid. This fluid flow is disturbed or increases in response to tactile, thermal (heat, or cold), and osmotic stimuli (high levels of sugar etc.), which is thought to result in a mechano-receptor response in the nerve fibers of the pulp, which is detected as pain. Nerve desensitizers and dentin tubule occluding agents have been used to treat teeth sensitivity. Special toothpastes, which contain potassium nitrate and/or bio-glass, amorphous calcium phosphate etc. are regularly used by consumers suffering from dentinal sensitivity. Another occluding agent that is also used to treat tooth sensitivity is potassium oxalate. However, none of these occluding agents are completely effective in mitigating the dentinal sensitivity, as effective occlusion on dentinal tubules is dependent on different variables. There is, therefore, a continuing need for tooth sensitivity treatment compositions, which have an improved affinity for dentin and effectively occlude dentinal tubules.

SUMMARY OF THE INVENTION

It has been discovered that the aforementioned objective can be achieved by selecting specific compounds which provide a protective barrier for teeth and/or effectively occlude exposed dentinal tubules and thereby decrease tooth sensitivity. In certain embodiments, the present invention provides an oral composition comprising:
  a) at least one compound of Formula I $$M^1\text{-}A\text{-}M^2\text{-}B\text{-}M^3 \quad (I)$$

wherein: $M^1$ and $M^3$ are, independently, a monovalent or divalent metal; $M^2$ is a polyvalent metal or metal oxide; and A and B are, independently, selected from the group consisting of $C_2$-$C_6$ diacids, triacids, and tetraacids;
  b) optionally, a flavor;
  c) optionally, a sweetener;
  d) optionally, a pH buffer; and
  e) at least one orally acceptable solvent,
wherein the oral composition has a pH of greater than (or at least) 2.0 (or about 2).

In other embodiments, the compositions of the present invention relate to an oral composition, comprising:
  a) at least one compound of Formula I $$M^1\text{-}A\text{-}M^2\text{-}B\text{-}M^3 \quad (I)$$

wherein: $M^1$ and $M^3$ are, independently, a monovalent or divalent metal; $M^2$ is a polyvalent metal or metal oxide; and A and B are, independently, selected from the group consisting of $C_2$-$C_6$ diacids, triacids, and tetraacids; and
  b) at least one orally acceptable solvent
wherein the composition is substantially free of water.

In still other embodiments, the compositions of the present invention relate to oral compositions comprising:
  a) at least one compound of Formula I $$M^1\text{-}A\text{-}M^2\text{-}B\text{-}M^3 \quad (I)$$

wherein: $M^1$ and $M^3$ are, independently, a monovalent or divalent metal; $M^2$ is a polyvalent metal or metal oxide; and A and B are, independently, selected from the group consisting of $C_2$-$C_6$ diacids, triacids, and tetraacids;
  b) at least one additional desensitizing agent; and
  c) at least one orally acceptable solvent.

In another embodiment, the compositions of the present invention relate to a method of treating sensitive teeth comprising the steps of applying to the sensitive teeth, for at least two consecutive applications, a composition comprising:
  a) at least one compound of Formula I $$M^1\text{-}A\text{-}M^2\text{-}B\text{-}M^3 \quad (I)$$

wherein: $M^1$ and $M^3$ are, independently, a monovalent or divalent metal; $M^2$ is a polyvalent metal or metal oxide; and A and B are, independently, selected from the group consisting of $C_2$-$C_6$ diacids, triacids, and tetraacids; and
  b) at least one orally acceptable solvent
wherein the applications are spaced no more than (or less than) 12 (or about 12) hours apart.

In still other embodiments, the compositions of the present invention relate to a method of occluding dentinal tubules of teeth comprising the steps of applying to the teeth, for at least two consecutive applications, a composition comprising:
  a) at least one compound of Formula I $$M^1\text{-}A\text{-}M^2\text{-}B\text{-}M^3 \quad (I)$$

wherein: $M^1$ and $M^3$ are, independently, a monovalent or divalent metal; $M^2$ is a polyvalent metal or metal oxide; and A and B are, independently, selected from the group consisting of $C_2$-$C_6$ diacids, triacids, and tetraacids; and
  b) contacting the teeth with the composition for at least (or greater than) 10 (or about 10) seconds
wherein the tubules are at least (or greater than) about 5% occluded.

In yet other embodiments, the compositions of the present invention relates to a method of occluding dentinal tubules of the teeth comprising the steps of applying to the teeth, for at least two consecutive applications, a composition comprising:
  a) at least one compound of Formula I $$M^1\text{-}A\text{-}M^2\text{-}B\text{-}M^3 \quad (I)$$

wherein: $M^1$ and $M^3$ are, independently, a monovalent or divalent metal; $M^2$ is a polyvalent metal or metal oxide; and A and B are, independently, selected from the group consisting of $C_2$-$C_6$ diacids, triacids, and tetraacids; and
  b) contacting the teeth with the composition in the presence of calcium for at least 20 seconds
wherein the compound forms a precipitate with the calcium on or in the vicinity of the teeth such that at least (or greater than) 30% (or about 30%) of the formed precipitate remains on the teeth after sonicating for 2 (or about 2) minutes.

In other embodiments, the compositions of the present invention relates to a method of depositing a precipitate on teeth and/or dentinal tubules of teeth comprising the steps of applying to the teeth, for at least two consecutive applications, a composition comprising:

a) at least one compound of Formula I

wherein: $M^1$ and $M^3$ are, independently, a monovalent or divalent metal; $M^2$ is a polyvalent metal or metal oxide; and A and B are, independently, selected from the group consisting of $C_2$-$C_6$ diacids, triacids, and tetraacids; and b) contacting the teeth with the composition in the presence of calcium for at least (or greater than) 20 (or about 20) seconds wherein $M^2$ is present in the precipitate at a concentration of at least (or greater than) 5% (or about 5%) of the deposited precipitate.

DETAILED DESCRIPTION OF THE INVENTION

Figure 1:
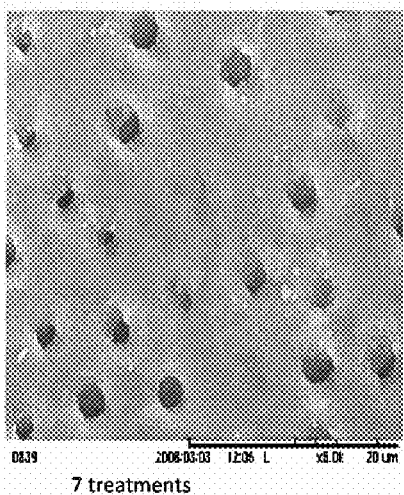
FIG. 1 is a scanning electron microscope image of an etched dentin chip taken after 7 treatments with 0.5% potassium oxalate formulation and showing minimal oxalate precipitation on dentin chip surface and/or dentin tubule occlusion after treatment.
Figure 2:
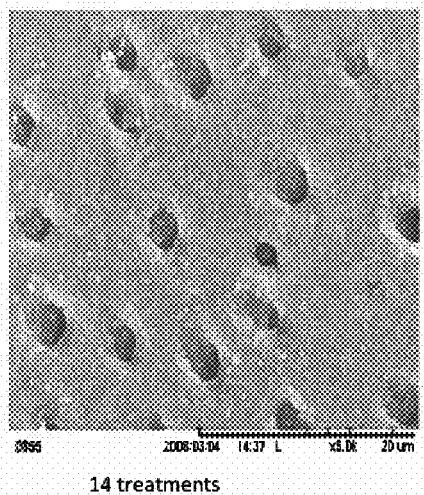
FIG. 2 is a scanning electron microscope image of an etched dentin chip taken after 14 treatments with 0.5% potassium oxalate formulation and showing minimal oxalate precipitation on dentin chip surface and/or dentin tubule occlusion after treatment.
Figure 3:
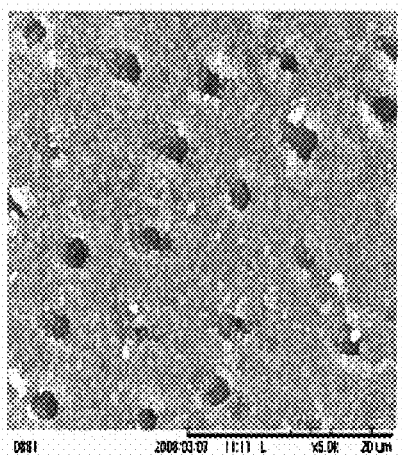
FIG. 3 is a scanning electron microscope image of an etched dentin chip taken after 21 treatments with 0.5% potassium oxalate formulation and showing minimal oxalate precipitation on dentin chip surface and/or dentin tubule occlusion after treatment.

The compositions of the present invention can comprise, consist of, or consist essentially of the essential elements and limitations of the invention described herein, as well any of the additional or optional ingredients, components, or limitations described herein.

All documents incorporated herein by reference in their entirety are only incorporated herein to the extent that they are not inconsistent with this specification.

All percentages, parts and ratios are based upon the total weight of the composition of the present invention, unless otherwise specified. All such weights as they pertain to the listed ingredients are based on the active level and, therefore, do not include carriers or by-products that may be included in commercially available materials, unless otherwise specified.

The term "safe and effective amount" as used herein means an amount of a compound or composition such as a topical or system active sufficient to significantly induce a positive benefit, for example, tooth desensitization, but low enough to avoid serious side effects, i.e., to provide a reasonable benefit to risk ratio, within the scope of sound judgment of the skilled artisan.

The term "occluded" or "occlusion" as used herein, means that the exposed openings of or into the dentin tubules are partially, substantially or completely obstructed.

The compositions of the present invention comprise at least one compound of Formula I

wherein: $M^1$ and $M^3$ are, independently, a monovalent or divalent metal; $M^2$ is a polyvalent metal or metal oxides thereof; and A and B are, independently, selected from the group consisting of $C_2$-$C_6$ diacids, triacids, and tetraacids, optionally $C_2$-$C_4$ diacids or triacids, optionally $C_2$-$C_3$ diacids or triacids, or optionally, $C_2$ diacids.

Examples of suitable monovalent metals include, but are not limited to Na, K and Li, optionally, Na or K, or optionally, K.

Examples of suitable divalent metals, include, but are not limited to, Mg, Ca, Sr, Ba, and Zn, optionally, Mg, Ba, and Zn, or optionally, Mg.

Examples of suitable polyvalent metals include, but are not limited to Ti, V, Cr, Mn, Fe, Co, Ni, Cu, Tc, Re, Os, Ir, Hg, Ce, Sn, Eu, Yb, Pa, and U, optionally, Ti, Sn, Mn, and Fe, or optionally Ti, Examples of suitable metal oxides include, but are not limited to, the corresponding oxides of Ba, Ti, V, Cr, Mn, Fe, Co, Ni, Cu, Tc, Re, Os, Ir, Hg, Ce, Sm, Eu, Yb, Pa, and U, optionally, the corresponding oxides of Ba, Ti, Sr, Sn, Zr, Mn, and Fe, optionally, the corresponding oxides of Ba, Ti, Sr, Sn, Zr, or optionally, the corresponding oxide of Ti, In certain embodiments, $M^1$ and/or $M^3$ are, independently, selected from the group consisting of Na, K, and Li. Optionally, both $M^1$ and $M^3$ are K.

In certain embodiments, $M^2$ is selected from the group consisting of Ti, Sr, Sn, Mg, Ca, Mn, and Zr. Optionally, $M^2$ is selected from the group consisting of oxides of Ti, Sr, Sn, Mg, Ca, Mn, and Zr. In other embodiments, $M^2$ is selected from the group consisting of Ti or oxide of Ti.

Examples of suitable diacids include, but are not limited to, oxalic acid, succinic acid, methylsuccinic acid, diglycolic acid, glutaric (i.e. pentanedioic) acid, 3,5,5-trimethylpentanedioic acid, hexanedioic acid, 3, 5,5-trimethylhexanedioic acid, 2,4,4-trimethylhexanedioic acid, decanedioic acid, undecanedioic acid, dodecanedioic acid, 1,4-cyclohexanedicarboxylic acid, cyclohexane-1,4-diacetic acid, maleic acid, citraconic acid, itaconic acid, fumaric acid, oxalic acid, terephthalic acid, phthalic acid, and isophthalic acid, hydroxysuccinic acid, malonic acid, adipic acid, sebacic acid, and tartaric acid, optionally, oxalic acid, succinic acid, or optionally, oxalic acid.

Examples of suitable triacids include, but are not limited to, citric acid.

Examples of suitable tetraacids include, but are not limited to, 1,1,2,2-ethanetetracarboxylic acid; 1,1,2,3-propanetetracarboxylic acid; 1,1,4,4-butanetetracarboxylic acid; 1,2,4,5-benzenetricarboxylic acid and ethylenediaminetetraacetic acid, or optionally, 1,1,2,2-ethanetetracarboxylic acid.

In certain embodiments, the compound of Formula I is selected from the group consisting of potassium titanium oxide oxalate ("KTO") (also referred to as potassium titanium oxalate), potassium titanium oxide citrate, calcium titanium oxalate, and potassium calcium titanium oxalate, optionally, potassium titanium oxide oxalate ("KTO"), potassium titanium oxide citrate or optionally, potassium titanium oxide oxalate ("KTO").

The compositions of the present invention include, based upon the total weight of the composition, from 0.01% (or about 0.01%) to 10.0% (or about 10.0%), optionally, from 0.1% (or about 0.1%) to 7.0% (or about 7.0%), or optionally, from 1% (or about 1%) to 5.0% (or about 5.0%) of at least one compound of Formula I.

In certain embodiments, the compositions of the invention include an orally acceptable solvent. Orally acceptable solvents include, but are not limited to, water; ethanol; n-propanol; or polyhydric alcohols such as glycerin, sorbitol, and polyethylene glycol; and any mixtures thereof and may be present at concentrations of from about 0.1% to about 99.9%, optionally, from about 1% to about 90%, or optionally, from about 10% to about 75% of the orally acceptable solvent.

In certain other embodiments, the compositions of the present invention are substantially free of water. By "substantially free", as used herein means less than 5% (or about 5%), optionally, less than 3% (or about 3%), optionally, less than 1% (or about 1%), optionally, less than 0.5% (or about 0.5%), optionally zero (or anhydrous).

In certain embodiments, the compositions of the present invention have a pH of at least 2 (or about 2), optionally, from 2.5 (or about 2.5) to 7.0 (or about 7.0), optionally, from 3.5 (or about 3.5) to 6.0 (or about 6.0), or optionally, from 3.2 (or about 3.2) to 4.5 (or about 4.5).

In certain embodiments, the pH of the compositions of the present invention may be buffered using conventional acid/salt systems. Common buffer systems include phosphoric acid and sodium phosphate salts, or citric acid and sodium citrate. Suitable acid/acid salt buffer combinations for use in this invention include citric acid-sodium citrate, phosphoric acid-sodium phosphate, sodium monobasic phosphate, sodium dibasic phosphate, acetic acid-sodium acetate, succinic acid-sodium succinate, aconitic acid-sodium aconitate and benzoic acid-sodium benzoate in amounts up to about 1% w/w, optionally from about 0.05% w/w to about 0.75% w/w of the composition, and or optionally from about 0.1% w/w to about 0.5% w/w of the composition.

Optional Components

In certain embodiments, the compositions of the present invention further include other tooth desensitizing agents. Examples of additional tooth desensitizing agents include, but are not limited to, potassium citrate, potassium chloride, potassium nitrate, citric acid, citric acid salts, strontium chloride, and mixtures thereof. Also, useful herein are the bioactive glass materials as described in U.S. Pat. Nos. 5,735,942; 5,891,233; 6,086,374; 6,244,871; 6,338,751; and 6,365,132, each of which are herein incorporated by reference in its entirety and phosphopeptides as described in U.S. Pat. Nos. 5,015,628; 5,981,475; 6,448,374; and 6,780,844, each of which are herein incorporated by reference in its entirety.

In certain embodiments, the additional tooth desensitizing agent is potassium nitrate. In certain embodiments, the concentration of the additional tooth desensitizing agent is from 0.1% (or about 0.01%) to 10% (or about 10%), optionally, from 0.1% (or about 0.1%) to 8% (or about 8%), or optionally, from 1% (or about 1%) to 7% (or about 7%) by weight of the composition.

Fluoride ion sources are well known for use in oral care compositions as anticaries actives and may also be incorporated into the compositions of the present invention. Fluoride ions are contained in a number of oral care compositions for this purpose, particularly toothpastes. Patents disclosing such toothpastes include U.S. Pat. Nos. 3,538,230; 3,689,637; 3,711,604; 3,911,104; 3,935,306; and 4,040,858, each of which are herein incorporated by reference in its entirety.

Application of fluoride ions to dental enamel serves to protect teeth against decay. A wide variety of fluoride ion-yielding materials can be employed as sources of soluble fluoride in the instant compositions. Examples of suitable fluoride ion-yielding materials are found in Briner et al; U.S. Pat. No. 3,535,421; issued Oct. 20, 1970 and Widder et al; U.S. Pat. No. 3,678,154; issued Jul. 18, 1972, both patents being incorporated herein by reference in their entirety. In certain embodiments, fluoride ion sources for use herein include stannous fluoride, monofluorophosphate, sodium fluoride, potassium fluoride and ammonium fluoride. In other embodiments sodium fluoride is incorporated. In certain embodiments, the compositions of the present invention provide from about 50 ppm to 10,000 ppm, optionally from about 100 to 3000 ppm, of fluoride ions in the aqueous solutions that contact dental surfaces.

Also useful in the compositions of the present invention are phosphates. Phosphates include pyrophosphates, polyphosphates, polyphosphonates and mixtures thereof. Pyrophosphates are among the best known for use in dental care products. Pyrophosphate ions are delivered to the teeth derive from pyrophosphate salts. The pyrophosphate salts useful in the present compositions include the dialkali metal pyrophosphate salts, tetra-alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In certain embodiments, tetrasodium pyrophosphate salt is the pyrophosphate.

The pyrophosphate salts are described in more detail in Kirk & Othmer, Encyclopedia of Clinical Technology Third Edition, Volume 17, Wiley-Interscience Publishers (1982), incorporated herein by reference in its entirety, including all references incorporated into Kirk & Othmer. Additional anticalculus agents include pyrophosphates or polyphosphates disclosed in U.S. Pat. No. 4,590,066; polyacrylates and other polycarboxylates such as those disclosed in U.S. Pat. Nos. 3,429,963; 4,304,766; and 4,661,341; polyepoxysuccinates such as those disclosed in U.S. Pat. No. 4,846,650; ethylenediaminetetraacetic acid as disclosed in British Patent No. 490, 384 dated Feb. 15, 1937; nitrilotriacetic acid and related compounds as disclosed in U.S. Pat. No. 3,678,154; polyphosphonates as disclosed in U.S. Pat. Nos. 3,737,533; 3,988,443; and 4,877,603; all of which cited patents are incorporated herein by reference in their entirety. In certain embodiments, phosphates include potassium and sodium pyrophosphates; sodium tripolyphosphate; diphosphonates, such as ethane-1-hydroxy-1,1-diphosphonate, 1-azacycloheptane-1,1-diphosphonate, and linear alkyl diphosphonates; tricalcium phosphates, linear carboxylic acids; sodium zinc citrate and mixtures of any of the above phosphates. In certain embodiments, the phosphate is tricalcium phosphate plus sodium lauryl sulfate as described in US 20080187500 A1, published Aug. 7, 2008 to Karlinsey, Robert L., which publication is hereby incorporated by reference in its entirety.

When incorporated into the compositions of the present invention, the phosphates can be present at concentrations of from about 0.01% to about 10%, optionally, from about 0.1% to about 7%, and, optionally, from about 0.5% to about 5%.

In certain embodiments, the compositions of the present invention also include essential oils. Essential oils are volatile aromatic oils that are synthetic or are derived from plants by distillation, expression or extraction. Essential oils usually carry the odor or flavor of the plant from which they are obtained. If used in the dentifrice compositions of this invention, essential oils provide anti-gingivitis activity. Some of these essential oils also act as flavoring agents. The essential oils of this invention include, but are not limited to, thymol, menthol, methyl salicylate (wintergreen oil) and eucalyptol.

Thymol, also known by the chemical formula 5-methyl 2-(1-methylethyl)phenol, is obtained from the essential oil of *Thymus vulgaris* Labiatae and *Monarda punctata* Labiatae. Thymol is a white crystalline powder with an aromatic odor and taste. Thymol is soluble in organic solvents but only slightly soluble in deionized water.

Menthol is isolated principally from the oil of *Mentha arvensis*. In its commercial form, menthol is available as L-menthol crystals obtained from a process involving cooling of the oil. Fractional distillation of peppermint oil that usually contains from about 40% to about 65% menthol represents another important source of menthol. Synthetic sources of L-menthol are also available.

Eucalyptol is derived from the eucalyptus tree. Having a camphoraceous odor and cooling taste, this essential oil is often combined with other essential oils such as menthol in confection formulations to impart medicinal effect. Combinations of menthol and eucalyptol are widely used. Particularly preferred uses of the menthol-eucalyptol combination include, according to the present invention, dentifrices such as toothpastes or dental gels.

Methyl salicylate is the main ingredient in many essential oils, constituting about 99% of oil of wintergreen (*Gaultheria procumbens*) and sweet birch (*Betula lenta*). Methyl salicylate, which has a distinctive refreshing aroma, is used widely in mouthwashes, chewing gums and other oral and pharmaceutical preparations.

The amounts of essential oils that can be used in the compositions of the present invention are from 0.001 (or about 0.001) to 1% (or about 1%) thymol, 0.001 (or about 0.001) to 1% (or about 1%) methyl salicylate, 0.001 (or about 0.001) to 15% (or about 15%) menthol and 0.001 (or about 0.001) to 1% (or about 1%) eucalyptol, wherein said amounts are clinically effective in inhibiting gingivitis. Optionally, a composition according to the present invention contains about 0.064% thymol, about 0.060% methyl salicylate, about 0.042% menthol and about 0.092% eucalyptol, wherein said amounts are clinically effective in inhibiting gingivitis.

Alternatively or in addition to the essential oils, the compositions of the present invention can also include an antimicrobially effective amount of an antimicrobial agent selected from the group consisting of polyphenols (e.g. triclosan) zinc salts, stannous fluoride, chlorhexidine, hexetidine, sanguinarine, benzalkonium chloride, salicylanilide, domiphen bromide, cetylpyridinium chloride, tetradecylpyridinium chloride (TPC), N-tetradecyl-4-ethylpyridinium chloride (TDEPC), octenidine, delmopinol, octapinol, and other piperidine derivatives, nicin preparations, zinc/stannous ion agents, antibiotics such as augmentin, amoxicillin, tetracycline, doxycycline, minocycline, and metronidazole, and analogs and salts of the above, essential oils including eugenol, geraniol, carvacrol, citral, hinokitiol, catechol, hydrogen peroxide, metal salts of chlorite, or any combination(s) of all of the above.

Mixtures of any of the above mentioned agents may also be used.

The compositions of the invention may also contain a surfactant selected from anionic, nonionic, amphoteric, betaine, cationic, and mixtures thereof. Suitable anionic surfactants include alkyl sulfates, alkyl ether sulfates, sulfosuccinates, isethionates, acyl amides, alkyl ether carboxylates and alkyl phosphates, wherein the alkyl group has from about 6 carbon atoms to about 30 carbon atoms. Suitable cationic surfactants include cetyl pyridinium chloride. The total amount of surfactant(s) that are suitable for use in the composition of the present invention may range from, based upon the total weight of the total composition, from about 1% to about 50%, optionally, from about 5% to about 40% or, optionally, from about 8% to about 25%.

Types of nonionic surfactants that are suitable for use in this invention include the fatty alcohol acid or amide ethoxylates, monoglyceride ethoxylates, sorbitan ester ethoxylates and alkyl polyglycosides. These normionic surfactants can be employed in composition of the present invention in an amount, based upon the total weight of the composition, from about 0.0% to about 30%, e.g. from about 0.1% to about 20% and from about 0.1% to about 15%.

Classes of amphoteric surfactants that are suitable for use in this invention include alkylimino-diproprionates, alkylamphoglycinates (mono or di), alkylamphoprionates (mono or di), alkylamphoacetates (mono or di), N-alkyl β-aminoproprionic acids, alkylpolyamino carboxylates, and phosphorylated imidazolines. These amphoteric surfactants can be employed in composition of the present invention in an amount, based upon the total weight of the composition, from about 0.1% to about 20%, e.g. from about 0.1% to about 15% and from about 0.1% to about 10%.

Types of betaines that are suitable for use in this invention include alkyl betaines, alkylamido betaines, alkyl sultaines and alkylamido sultaines, wherein the alkyl group has from about 6 carbon atoms to about 30 carbon atoms, with about 10 to about 14 carbon atoms being preferred. These betaine surfactants can be employed in the composition of the present invention in an amount, based upon the total weight of the cleansing composition, from about 0.1% to about 15%, e.g. from about 0.1% to about 10% and from about 0.1% to about 8%.

Classes of cationic surfactants that are suitable for use in this invention include alkyl quaternaries (mono, di, or tri), benzyl quaternaries (e.g. cetyl pyridinium chloride), ester quaternaries, ethoxylated quaternaries, alkyl amines, and mixtures thereof, wherein the alkyl group has from about 6 carbon atoms to about 30 carbon atoms, with about 8 to about 22 carbon atoms being preferred. These cationic surfactants can be employed in composition of the present invention in an amount, based upon the total weight of the composition, from about 0.01% to about 20%, optionally from about 0.05% to about 15% and or optionally from about 0.1% to about 10%.

The compositions of the present invention may also include one or more optional ingredients nonexclusively including a thickening agent, humectants, chelating agents and additives such as flavorants, preservatives, and the like.

Commercially available thickening agents, which are capable of imparting the appropriate viscosity to the compositions, are suitable for use in this invention. Examples of suitable thickening agents nonexclusively include: mono or diesters of 1) polyethylene glycol of formula: HO—$(CH_2CH_2O)_z$H, wherein z is an integer from about 3 to about 200; and 2) fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; and mixtures thereof. Preferred thickeners include polyethylene glycol ester, and more preferably PEG-150 distearate which is available from the Stepan Company of Northfield, Ill. or from Comiel, S.p.A. of Bologna, Italy under the tradename, "PEG 6000 DS".

In certain embodiments, thickening agents can be included in the compositions of the present invention at concentrations of from about 0.01% to about 10%, optionally, from about 0.1 to about 5%, or optionally, from about 0.2% to about 2.0%.

Commercially available humectants are suitable for use in the present invention for their humectant properties in addition to their use as a potential solvents as detailed above. The humectant may be present in an amount of from about 0% to about 10%, preferably from about 0.5% to about 5%, and more preferably from about 0.5% to about 3%, based on the overall weight of the composition. Examples of suitable humectants nonexclusively include: 1) water soluble liquid polyols selected from the group comprising glycerine, propylene glycol, hexylene glycol, butylene glycol, dipropylene glycol, and mixtures thereof; 2) polyalkylene glycol of the formula: HO—$(R''O)_b$—H, wherein R'' is an alkylene group having from about 2 to about 3 carbon atoms and b is an integer of from about 2 to about 10; 3) polyethylene glycol ether of methyl glucose of formula $CH_3$—$C_6H_{10}O_5$—$(OCH_2CH_2)_c$—OH, wherein c is an integer from about 5 to about 25; 4) urea; and 5) mixtures thereof, with glycerine being the preferred humectant.

In certain embodiments, humectants can be incorporated into the compositions of the present invention at concentrations of from about 0.1% to about 40%, optionally, from about 1.0% to about 30%, or optionally, from about 5% to about 25%.

In certain embodiments, chelating agents can be incorporated into the compositions of the present invention. Examples of suitable chelating agents include those which are capable of protecting and preserving the compositions of this invention. Optionally, in addition to its potential use as a tetraacid in the compound(s) of Formula I, ethylenediamine tetracetic acid ("EDTA") may be used as the chelating agent. In certain embodiments, the chelating agent is tetrasodium EDTA, available commercially from Dow Chemical Company of Midland, Mich. under the tradename, "Versene 100XL" and may be present in an amount, based upon the total weight of the composition, of from about 0 to about 0.5%, and optionally from about 0.05% to about 0.25%.

Suitable preservatives include, sodium benzoate, and polysorabate and are present in the composition in an amount, based upon the total weight of the composition, from about 0 to about 0.2%, and preferably from about 0.05% to about 0.10%.

The compositions of the present invention may be in the form of mouthwashes, mouthrinses, dentifrices, pastes such as toothpastes, powders such as toothpowders, gels, tablets, lozenges, microcapsules, sprays, varnishes or strips (such as remineralization strips as disclosed in US patent publication 20070128130 to Kropt et al. published Jun. 7, 2007, herein incorporated by reference in its entirety or, peroxide or non-peroxide tooth whitening strips as disclosed in US patent publication 20080003248 to Georgiades et al. published Jan. 3, 2008 and U.S. Pat. No. 6,949,240 to Sagel et al. issued Sep. 27, 2005, both of which patent documents are herein incorporated by reference in their entirety), coatings for such strips and the like. As alluded to above, the compositions of the present invention can also be applied by conventional oral care devices, including toothbrushes, dental pics, dental floss, dental sprayers or misters and dental pens as described in US patent publication 20080044363 to Montgomery, published Feb. 21, 2008, herein incorporated by reference in its entirety.

The compositions of the present invention can also be useful as a coating for or as an impregnant for impregnation into dental devices selected from the group consisting of toothbrushes (manual or mechanical), toothbrush bristles, dental floss, dental pics and the like. The compositions of the present invention can also be useful as coatings or impregnants for dental composite materials, dental fillings and the like.

Method of Using the Compositions of the Present Invention

The invention illustratively disclosed herein may be practiced in the absence of any component, ingredient, or step which is not specifically disclosed herein.

In certain embodiments, the compositions of the present invention are applied to sensitive teeth, for at least two consecutive applications, optionally, at least (or greater than) 7 (or about 7) consecutive applications, or optionally, 14 (or about 14) consecutive applications, or optionally, 21 (or about 21) consecutive applications, or optionally, 28 (or about 28) consecutive applications.

When applied to a sensitive tooth (or teeth), in certain embodiments, the composition is allowed to remain in contact with the sensitive teeth for at least (or greater than) 10 (or about 10) seconds, optionally 20 (or about 20) seconds, optionally 30 (or about 30) seconds, optionally 50 (or about 50) seconds, or optionally 60 (or about 60) seconds.

In certain embodiments, the time between consecutive applications should be no more than (or less than) 12 (or about 12) hours apart, optionally, 8 (or about 8) hours apart, optionally, 4 (or about 4) hours apart, optionally, 2 (or about 2) hours apart, or optionally, one (or about one) hour apart.

In certain embodiments, the compositions of the present invention are applied to the sensitive teeth such that the compounds of Formula I form precipitate deposits with available calcium on the teeth such that at least (or greater than) 5% (or about 5%) of the teeth's dentin tubules are occluded, optionally 25% (or about 25%) of the dentin tubules are occluded, optionally 40% (or about 40%) of the dentin tubules are occluded, optionally 60% (or about 60%) of the dentin tubules are occluded, optionally 75% (or about 75%) of the dentin tubules are occluded, optionally 85% (or about 85%) of the dentin tubules are occluded, or optionally 95% (or about 95%) of the dentin tubules are occluded.

In certain embodiments, the $M^2$ of Formula I is present in the precipitate deposit formed by the compound(s) of Formula I and calcium at a concentration of at least (or greater than) 5% (or about 5%), optionally 10% (or about 10%), optionally 20% (or about 20%), or optionally 35% (or about 35%).

Once formed on the teeth, the stability of precipitate deposit(s) comprising the compounds Formula I and calcium provide is such that at least (or greater than) 5% (or about 5%), optionally 30% (or about 30%), optionally 35% (or about 35%), optionally 50% (or about 50%), optionally 75% (or about 75%), or optionally 90% (or about 90%) remain on the teeth after sonication for 2 (or about 2) minutes using an ultra sonicator CD-4800 (Digital Professional Ultrasonic Cleaner [CD-4800], manufactured by Best And More Electronics [Shenzhen] Co., Ltd., China) at normal pulse of about 42 KHz. At this pulse, the sonicator generally provides a force greater than that typically used in sonic or manual tooth brushing. The phrase "precipitate deposit(s)", as used herein means the deposit formed on the teeth and/or which occludes the tubules of the teeth by precipitation of the compound(s) of Formula I with calcium present in the fluids of the oral cavity after application of compositions comprising the compound(s) of Formula I as disclosed in the present application. Formation of the precipitate deposit(s) with the compound(s) of Formula I may also be generated or facilitated by separately adding calcium to the oral cavity in the form of water-soluble calcium salts before or after addition of the compositions of the present invention comprising the compound(s) of Formula I. Examples of suitable water-soluble calcium salts include, but are not limited to calcium chloride, calcium nitrate, calcium bromide, and calcium dihydrogenphosphate and mixtures thereof. The amount of the water-soluble calcium salt should exceed, on a molar basis, the amount of the compound(s) of Formula I provided by the compositions of the present invention.

Several examples are set forth below to further illustrate the nature of the invention and the manner of carrying it out.

EXAMPLES

The compositions of the present invention as described in following examples illustrate specific embodiments of compositions of the present invention, but are not intended to be limiting thereof. Other modifications can be undertaken by the skilled artisan without departing from the spirit and scope of this invention.

Preparation of Mouthrinse Formulations

Liquid mouth rinse formulations were prepared and the dentin occluding efficacy of potassium titanium oxide oxalate (KTO) formulations was evaluated. The method of preparation is described as follows:

In a formulation vessel, water, KTO, benzoic acid, and poloxamer was added and mixed until dissolved. Once poloxamer was dissolved, the alcohol, n-propanol, sorbitol and water were added, followed by sodium benzoate and then mixed until dissolved. The pH was checked and determined to be about 4.2.

To the above formulation mixture, menthol, thymol, eucalyptol, methyl salicylate were added and mixed until homogenous. Once a homogenous solution is formed, sodium saccharin and FDC green #3 (1% solution, purity adjusted) were added. The formulation was mixed until homogeneous. The final pH of the formulation was 4.2.

The composition of the liquid mouthrinse formulations are described in Table 1.

TABLE 1

| Ingredient | A % wt | B % wt | C % wt | D % wt | E % wt |
|---|---|---|---|---|---|
| Alcohol USP | 22.653 | 22.653 | 22.653 | 22.653 | 22.653 |
| Menthol USP | 0.032 | 0.032 | 0.032 | 0.032 | 0.032 |
| Thymol NF | 0.064 | 0.064 | 0.064 | 0.064 | 0.064 |
| Methyl Salicylate NF | 0.066 | 0.066 | 0.066 | 0.066 | 0.066 |
| Eucalyptol USP | 0.092 | 0.092 | 0.092 | 0.092 | 0.092 |
| n-Propanol | 0.500 | 0.500 | 0.500 | 0.500 | 0.500 |
| Mint Flavor N & A | 0.085 | 0.085 | 0.085 | 0.085 | 0.085 |
| Poloxamer 407 | 0.250 | 0.250 | 0.250 | 0.250 | 0.250 |
| Benzoic Acid, USP | 0.120 | 0.120 | 0.120 | 0.120 | 0.120 |
| Sodium Benzoate | 0.035 | 0.035 | 0.035 | 0.035 | 0.035 |
| Potassium oxalate (KO) | 0.100 | 0.5 | 0.000 | 0.000 | 0.000 |
| Potassium Titanium oxide Oxalate( KTO) | 0.000 | 0.000 | 0.100 | 0.500 | 0.000 |
| Saccharin Sodium USP | 0.117 | 0.117 | 0.117 | 0.117 | 0.117 |
| FD&C Green #3 | 0.001 | 0.001 | 0.001 | 0.001 | 0.001 |
| Sorbitol Solution USP | 20.000 | 20.000 | 20.000 | 20.000 | 20.000 |
| Purified Water, USP | 55.885 | 55.485 | 55.885 | 55.485 | 55.985 |
| TOTAL | 100.000 | 100.000 | 100.000 | 100.000 | 100.000 |
| pH | 4.2 | 4.2 | 4.2 | 4.2 | 4.2 |

Preparation of Dentin Samples and Artificial Saliva

Dentin occlusion efficacy of the KTO compounds and formulations of the present invention was demonstrated as follows:

Dentin chips (polished and unetched) were obtained from Dental product testing, Division of Thermametric technologies Inc., Indianapolis, Ind., USA. The dentin chips were etched to completely remove the smear layer (or, debris layer caused by cutting the dentin or enamel) by soaking the dentin chips in 6% citric acid for up to 2 minutes followed by rinsing and sonication in deionized water.

Potassium oxalate (KO) was obtained from Fluka, St. Louis, Mo., (lot#: 430462/1). Potassium titanium oxide oxalate (KTO) dihydrate was obtained from Sigma, St. Louis Mo. (lot# 51740).

Artificial saliva was prepared using conventional equipment and protocols routinely used in laboratory protocols and having the composition as shown in Table 2:

TABLE 2

| Ingredient | Concentration |
|---|---|
| Sodium Chloride | 0..381 g/L |
| Calcium Chloride di-hydrate | 0.213 g/L |
| Potassium dihydrogen phosphate | 0.738 g/L |

TABLE 2-continued

| Ingredient | Concentration |
|---|---|
| Potassium Chloride | 1.114 g/L |
| Gastric Mucin | 2.20 g/L | pH = 7.0

Comparison Testing and Analysis

All the etched dentin chip samples (10 in total) were randomized and divided into five treatment groups. Scanning electron microscopy (SEM) and surface chemical analysis using Electron dispersive spectroscopy (EDS) were preformed to monitor tubule occlusion and surface deposition generated by the KTO formulations. The five treatment groups were as follows:

Group 1: Treated with formulation A
Group 2: Treated with formulation B
Group 3: Treated with formulation C
Group 4: Treated with formulation D
Group 5: Treated with formulation E (i.e., no KTO nor KO)

The treatment regimen for the Groups 1-5 consisted of the following:
1. Treating the chip samples in each group with 20 mls of respective treatment formulation, with shaking, for 30 seconds.
2. Rinsing the chip samples in each group with deionized $H_2O$ for 1 minute.
3. Immersing the chip samples in the artificial saliva composition between treatments, and no more than two treatments were carried per day.
4. Repeating steps 1-3 for a total 28 treatments.
5. Dentin specimens were analyzed by SEM and/or EDS after 7, 14, 21 and 28 treatments. Before analysis the chips were rinsed with deionized $H_2O$ for 3 minutes and air dried for SEM analysis.

The data obtained from EDS analysis of the 2 chip samples per group (Chip 1 and Chip 2) is summarized in Tables 3 and 4 below.

TABLE 3

EDS after 7 Treatments

| Formulation | | S (%) | K (%) | P (%) | Ca (%) | Ti (%) |
|---|---|---|---|---|---|---|
| A | Chip 1 | 39.0 | 5.4 | 12.5 | 43.1 | X |
|   | Chip 2 | 37.9 | 6.2 | 13.5 | 42.4 | X |
| B | Chip 1 | 16.9 | 9.3 | 17.2 | 56.6 | X |
|   | Chip 2 | 17.7 | 9.7 | 18.0 | 54.6 | X |
| C | Chip 1 | 5.7 | 12.0 | 21.7 | 34.6 | 26.0 |
|   | Chip 2 | 4.6 | 12.4 | 19.6 | 35.2 | 28.2 |
| D | Chip 1 | X | 11.6 | 28.0 | 28.3 | 32.1 |
|   | Chip 2 | X | 12.5 | 25.7 | 33.3 | 28.5 |
| E | Chip 1 | 48.2 | X | 13.0 | 38.8 | X |
|   | Chip 2 | 47.7 | X | 13.2 | 39.1 | X |

TABLE 4

EDS after 14 Treatments

| Formulation | | S (%) | K (%) | P (%) | Ca (%) | Ti (%) |
|---|---|---|---|---|---|---|
| A | Chip 1 | 30.6 | 8.4 | 12.5 | 48.5 | X |
|   | Chip 2 | 29.5 | 9.0 | 11.3 | 50.2 | X |
| B | Chip 1 | 6.8 | 13.5 | 16.0 | 60.5 | X |
|   | Chip 2 | 8.7 | 15.4 | 18.4 | 57.5 | X |
| C | Chip 1 | 1.8 | 10.2 | 27.4 | 26.3 | 26.7 |
|   | Chip 2 | 2.1 | 11.7 | 29.4 | 25.8 | 28.4 |
| D | Chip 1 | X | 18.7 | 22.1 | 26.4 | 32.8 |
|   | Chip 2 | X | 20.9 | 17.7 | 30.0 | 31.4 |
| E | Chip 1 | 47.5 | X | 13.6 | 38.9 | X |
|   | Chip 2 | 48.1 | X | 12.7 | 39.2 | X |

After 7 treatments, 0.5% KTO (Formulation D) treated samples show the highest affinity for etched dentin surface as is evident from the reduction of the percent sulfur detected in the EDS reading (EDS spectra of etched to dentin surface typically shows about 45-50% Sulfur). The percent sulfur detected is reduced as the sulfur on the dentin chip surface becomes covered or masked by the surface deposition generated by the KTO formulation treatments. While not completely absent, the percent sulfur detected is dramatically reduced in the 0.1% KTO (Formulation C) treated sample. After 14 treatments, the percent sulfur detected remained low in the 0.5% KTO (Formulation D) treated sample and more significantly reduced in the 0.1% KTO (formulation C) treated sample.

Scanning electron microscopy carried out on these samples suggests the initiation or formation of surface precipitation on the dentin surface for Formulation D samples, and the degree of tubule occlusion increases with number of treatments.

SEM analysis, image grading, and calculation of percent tubule occlusion was carried out to obtain a semi-quantitative comparison of dentin tubule occlusion efficacy of different formulations. The methods and calculations for analyzing SEM data, grading images and obtaining percent tubule occlusion were carried out in accordance with methods described in West N X, Addy, M, Hughes, J. (1998) J. Oral Rehabil, 25, 885 and confirm by the methods describes in Lee S Y, Kwon H K, Kim B I (2008) J. Oral Rehabil, 35, 847. Based on the above described analysis of the SEM data, the percent tubule occlusion was determined for Formulations A-E at treatments 7, 14, 21 and 28 is summarized in Table 5.

TABLE 5

Percentage tubule occlusion

| Formulation | 7 treatment | 14 treatment | 21 treatment | 28 treatment |
|---|---|---|---|---|
| A | 5% | 15% | 25% | 40% |
| B | 20% | 35% | 45% | 60% |
| C | 25% | 35% | 55% | 75% |
| D | 40% | 65% | 85% | >99% |
| E | 0% | 5% | 5% | 5% |

A comparison analyzed data for pre-(prior to treatments) and post treatment scanning electron micrographs at different times in treatment cycle and different KTO concentrations (as illustrated in Table 5 and FIGS. 1 through 4 (KO treatment), 5 through 8 (KTO treatment) and 9 and 10 (no oxalate treatment) clearly demonstrate increased surface precipitation leading to enhanced and effective increase in tubule occlusion.

Substantivity Determination for Formed Precipitate Deposits

Figure 4:
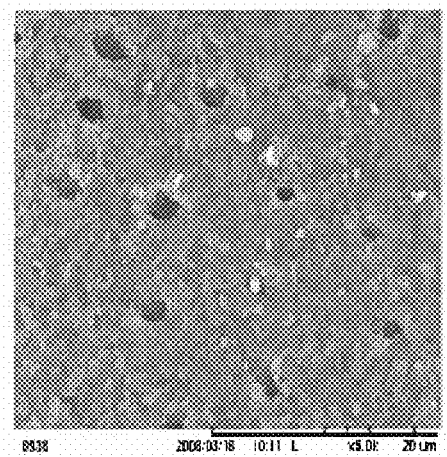
FIG. 4 is a scanning electron microscope image of an etched dentin chip taken after 28 treatments with 0.5% potassium oxalate formulation and showing minimal oxalate precipitation on dentin chip surface and/or dentin tubule occlusion after treatment.
Figure 5:
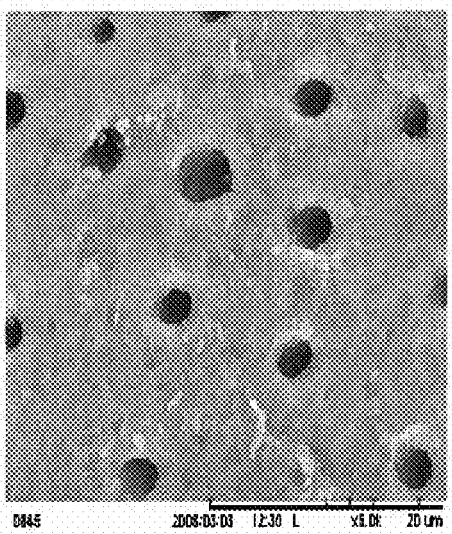
FIG. 5 is a scanning electron microscope image of an etched dentin chip taken after 7 treatments with 0.5% potassium titanium oxide oxalate formulation and showing substantial titanium oxide oxalate precipitation on dentin chip surface and/or virtually complete dentin tubule occlusion after treatment.
Figure 6:
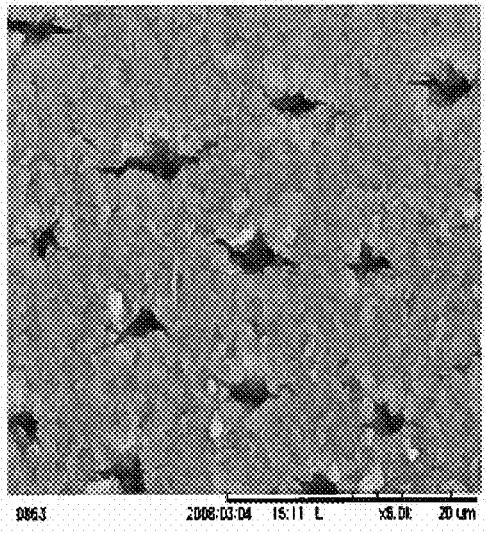
FIG. 6 is a scanning electron microscope image of an etched dentin chip taken after 14 treatments with 0.5% potassium titanium oxide oxalate formulation and showing substantial titanium oxide oxalate precipitation on dentin chip surface and/or virtually complete dentin tubule occlusion after treatment.
Figure 7:
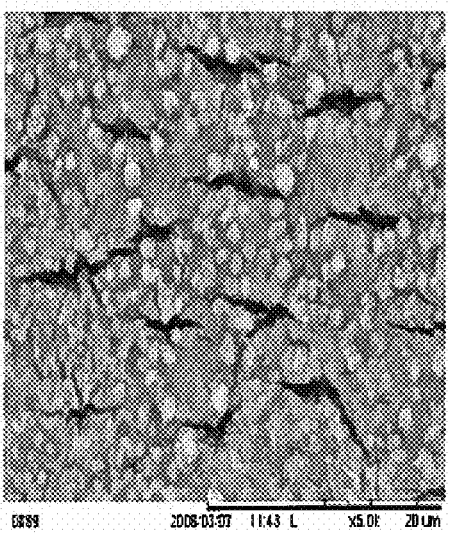
FIG. 7 is a scanning electron microscope image of an etched dentin chip taken after 21 treatments with 0.5% potassium titanium oxide oxalate formulation and showing substantial titanium oxide oxalate precipitation on dentin chip surface and/or virtually complete dentin tubule occlusion after treatment.
Figure 8:
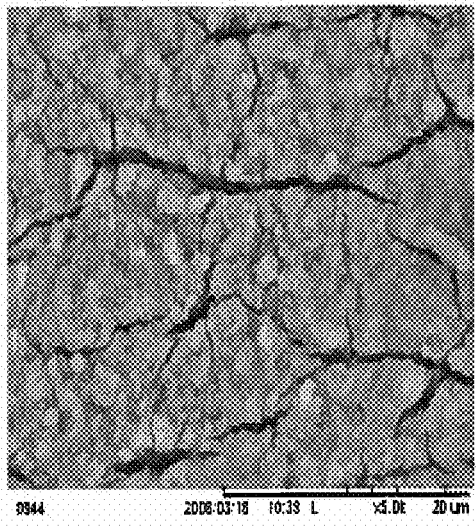
FIG. 8 is a scanning electron microscope image of an etched dentin chip taken after 28 treatments with 0.5% potassium titanium oxide oxalate formulation and showing substantial titanium oxide oxalate precipitation on dentin chip surface and/or virtually complete dentin tubule occlusion after treatment.
Figure 9:
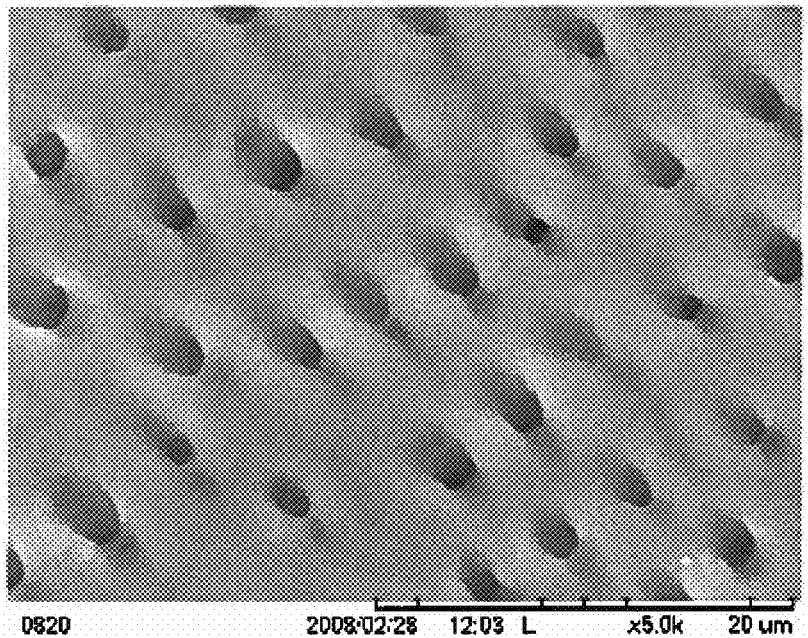
FIG. 9 is a scanning electron microscope image of an etched dentin chip taken before treatment with a formulation having the same ingredients as that used the treat the dentin chips of FIGS. 1 through 8, but containing no potassium oxalate or potassium titanium oxide oxalate and showing no change in precipitation on dentin chip surface and/or dentin tubule occlusion prior to treatment and after treatment.
Figure 10:
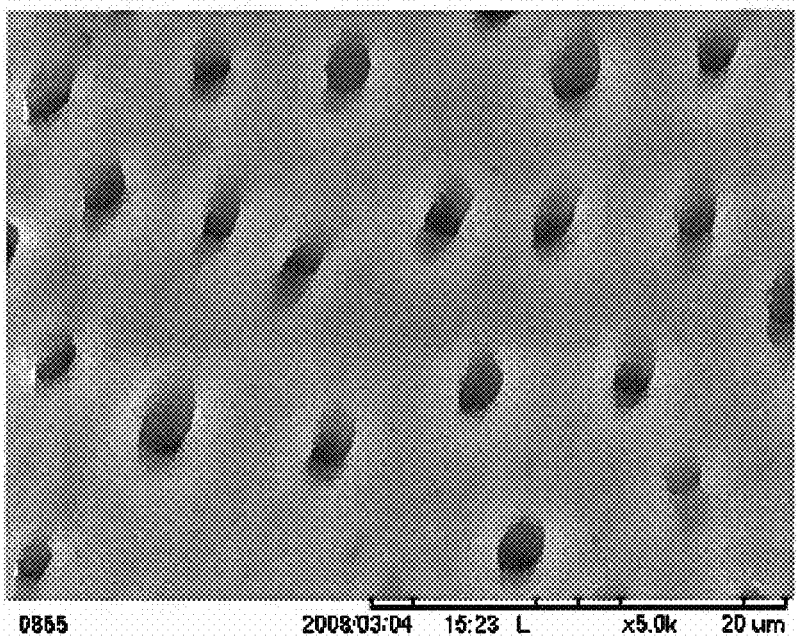
FIG. 10 is a scanning electron microscope image of an etched dentin chip taken after 28 treatment with a formulation having the same ingredients as that used the treat the dentin chips of FIGS. 1 through 8, but containing no potassium oxalate or potassium titanium oxide oxalate and showing no change in precipitation on dentin chip surface and/or dentin tubule occlusion prior to treatment and after treatment.
Figure 11:
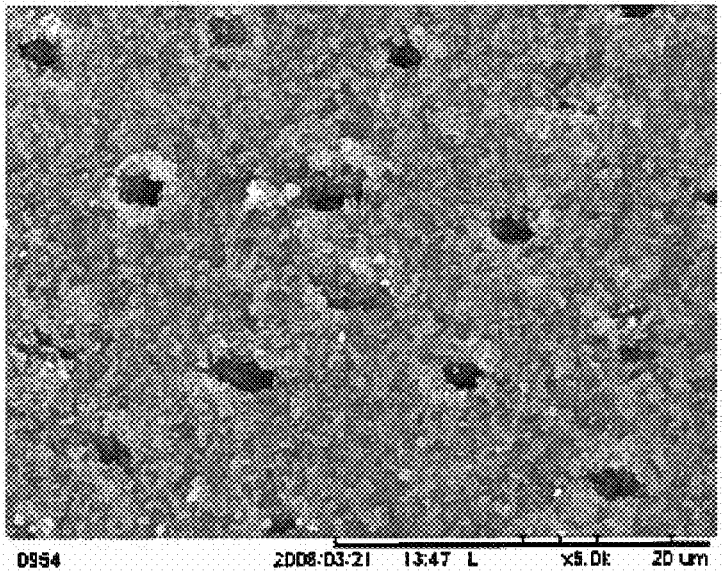
FIG. 11 is a scanning electron microscope image of an etched dentin chip having undergone 28 treatments with a formulation containing 0.5% potassium oxalate (Formulation B) and then sonicated for 2 minutes using a sonicater at normal pulse.
Figure 12:
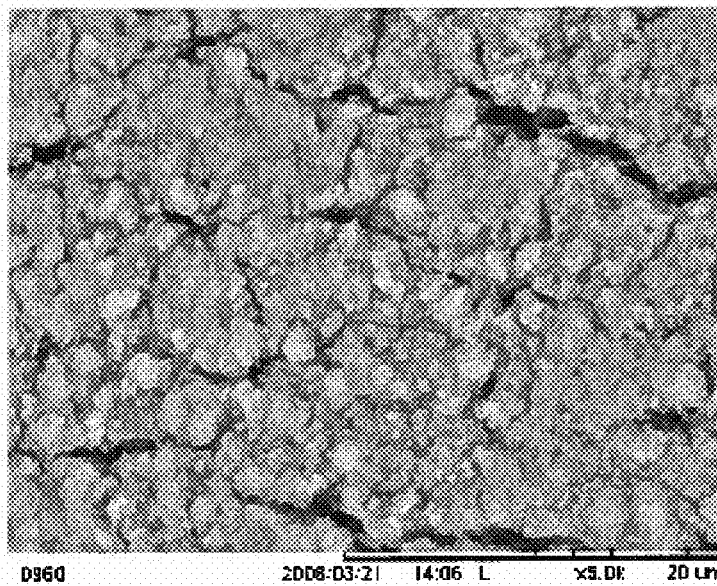
FIG. 12 is a scanning electron microscope image of an etched dentin chip having undergone 28 treatments with a formulation containing 0.5% potassium titanium oxide oxalate (Formulation D) and then sonicated for 2 minutes using a sonicater at normal pulse. Comparison of these dentin chips images in FIGS. 11 and 12 with their respective 28 day treatment image as depicted in FIGS. 4 and 8 illustrate the increased stability of the precipitates generated by potassium titanium oxide oxalate formulation versus the potassium oxalate formulation.

The following was performed to determine the substantivity (or, ability of the precipitate to remain on the dental surface) of the KTO precipitate deposited on dentin chip samples during the treatment cycle. The dentin chips treated with Formulation B (0.5% KO) and Formulation D (0.5% KTO)

for 28 treatments were sonicated for 2 minutes (about 2 minutes can also be used) using an ultra sonicator CD-4800 at normal pulse (about 42 KHz). Comparison of the images of the sonicated chips (FIGS. 11 and 12) with their respective 28 day treatment images as depicted in FIGS. 4 and 8 demonstrate that the KTO generated precipitate deposits were more resistant to the sonication (about 92% of KTO generated precipitate remained on chip sample) than the KO generated precipitates (about 38% of KO generated precipitate remained on chip sample) indicating that the KTO generated precipitate deposits provide increased stability versus the KO generated precipitate deposits. Without being limited by theory, it is believed that this improved stability of the precipitate deposits generated by the compounds of Formula I, not only provide a greater degree of tooth desensitization, but longer lasting tooth desensitization as well.

Tables 6 and 7 provide Examples F-O illustrating additional mouthwash examples of compositions of the present invention. Examples F-O can be prepared in the manner outlined for Examples A-E above.

TABLE 6

| | F<br>% wt | G<br>% wt | H<br>% wt | I<br>% wt | J<br>% wt |
|---|---|---|---|---|---|
| Alcohol USP | 22.653 | 22.653 | 22.653 | 22.653 | 22.653 |
| Menthol USP | 0.032 | 0.032 | 0.032 | 0.032 | 0.032 |
| Thymol NF | 0.064 | 0.064 | 0.064 | 0.064 | 0.064 |
| Methyl Salicylate NF | 0.066 | 0.066 | 0.066 | 0.066 | 0.066 |
| Eucalyptol USP | 0.092 | 0.092 | 0.092 | 0.092 | 0.092 |
| n-Propanol | 0.500 | 0.500 | 0.500 | 0.500 | 0.500 |
| Mint Flavor N & A | 0.085 | 0.085 | 0.085 | 0.085 | 0.085 |
| Poloxamer 407 | 0.250 | 0.250 | 0.250 | 0.250 | 0.250 |
| Benzoic Acid, USP | 0.120 | 0.120 | 0.120 | 0.120 | 0.120 |
| Sodium Benzoate | 0.035 | 0.035 | 0.035 | 0.035 | 0.035 |
| Potassium Titanium Oxide Citrate | 0.100 | 0.5 | — | — | — |
| Calcium Titanium Oxalate | — | — | 0.100 | 0.500 | — |
| Potassium Titanium Oxide Oxalate | | | | | 2.00 |
| Saccharin Sodium USP | 0.117 | 0.117 | 0.117 | 0.117 | 0.117 |
| FD&C Green #3 | 0.001 | 0.001 | 0.001 | 0.001 | 0.001 |
| Sorbitol Solution USP | 20.000 | 20.000 | 20.000 | 20.000 | 20.000 |
| Purified Water, USP | 55.885 | 55.485 | 55.885 | 55.485 | 53.485 |
| TOTAL | 100.00 | 100.00 | 100.00 | 100.00 | 100.000 |
| pH | 4.2 | 4.2 | 4.2 | 4.2 | 4.2 |

TABLE 7

| | K<br>% wt | L<br>% wt | M<br>% wt | N<br>% wt | O<br>% wt |
|---|---|---|---|---|---|
| Alcohol USP | 22.653 | 22.653 | 22.653 | 22.653 | 22.653 |
| Menthol USP | 0.032 | 0.032 | 0.032 | 0.032 | 0.032 |
| Thymol NF | 0.064 | 0.064 | 0.064 | 0.064 | 0.064 |
| Methyl Salicylate NF | 0.066 | 0.066 | 0.066 | 0.066 | 0.066 |
| Eucalyptol USP | 0.092 | 0.092 | 0.092 | 0.092 | 0.092 |
| Mint Flavor N & A | 0.085 | 0.085 | 0.085 | 0.085 | 0.085 |
| Poloxamer 407 | 0.250 | 0.250 | 0.250 | 0.250 | 0.250 |
| Benzoic Acid, USP | 0.120 | 0.120 | 0.120 | 0.120 | 0.120 |
| Sodium Benzoate | 0.035 | 0.035 | 0.035 | 0.035 | 0.035 |
| Potassium Titanium Oxide Oxalate | 0.100 | 0.500 | 0.5 | 1.0 | 2.0 |
| Potassium Nitrate | 2.4 | 2.4 | 3.0 | 3.0 | 3.0 |
| Saccharin Sodium USP | 0.117 | 0.117 | 0.117 | 0.117 | 0.117 |
| FD&C Green #3 | 0.001 | 0.001 | 0.001 | 0.001 | 0.001 |
| Sorbitol Solution USP | 20.000 | 20.000 | 20.000 | 20.000 | 20.000 |
| Purified Water, USP | 53.210 | 52.810 | 52.210 | 52.710 | 51.710 |
| TOTAL | 100.00 | 100.00 | 100.00 | 100.00 | 100.000 |
| pH | 4.2 | 4.2 | 4.2 | 4.2 | 4.2 |

Table 8 provides Examples P-S illustrating dentifrice examples of compositions of the present invention. Examples P-S can be prepared using conventional dentifrice mixing technology. Example S illustrates an anhydrous dentifrice embodiment of the present invention.

TABLE 8

| Ingredients | P<br>(% w/w) | Q<br>(% w/w) | R<br>(% w/w) | S<br>(% w/w) |
|---|---|---|---|---|
| Water | 15.00 | 12.50 | 10.00 | — |
| Glycerin 99.7%, USP | 23.00 | 23.00 | 23.00 | 28.00 |
| Sodium Carboxymethylcellulose | 0.60 | 0.60 | 0.60 | 0.60 |
| Sorbitol (70%) | 24.96 | 24.96 | 24.96 | 29.96 |
| Sodium Saccharin | 0.20 | 0.20 | 0.20 | 0.20 |
| Sucralose | 0.80 | 0.80 | 0.80 | 0.80 |
| Sodium Fluoride | 0.24 | 0.24 | 0.24 | 0.24 |
| Hydrated Silica | 20.00 | 20.00 | 20.00 | 20.00 |
| Potassium Nitrate | 0.00 | 5.00 | 5.00 | 5.00 |
| potassium titanium oxalate (KTO) | 5.00 | 2.50 | 5.00 | 5.00 |
| Synthetic Amorphous Silica | 6.50 | 6.50 | 6.50 | 6.50 |
| Sodium Lauroyl Sarcosinate | 1.00 | 1.00 | 1.00 | 1.00 |
| Lauryl Glucoside | 1.00 | 1.00 | 1.00 | 1.00 |
| Cocamidopropyl betaine | 0.50 | 0.50 | 0.50 | 0.50 |
| Flavor | 1.20 | 1.20 | 1.20 | 1.20 |
| Total | 100.00 | 100.00 | 100.00 | 100.00 |

What is claimed is:

1. A tooth sensitivity treatment composition comprising:
a) at least one compound of Formula I $$M^1\text{-}A\text{-}M^2\text{-}B\text{-}M^3 \qquad (I)$$

wherein: $M^1$ and $M^3$ are, independently, a monovalent or divalent metal; $M^2$ is a polyvalent metal oxide or a polyvalent metal selected from the group consisting of Ti, Sr, Mg, Ca, Mn, and Zr; and A and B are, independently, selected from the group consisting of $C_2$-$C_6$ diacids, triacids, and tetraacids;

b) water; and c) at least one or more of an ingredient selected from the group consisting of humectants, chelating agents, thickening agents, flavorants sweeteners and preservatives, wherein the compound is dissolved in the water and is in an effective amount to induce tooth desensitization; and wherein the tooth sensitivity treatment composition has a pH of about 3.2 to about 4.5, provided that, if chelating agents are present, they are present at a level of from about 0.05% to about 0.25%.

2. The composition according to claim 1, wherein $M^1$ and $M^3$ are, independently, a monovalent metal selected from the group consisting of Na, K, and Li.

3. The compositions according to claim 2, wherein the $M^1$ and $M^3$ are K.

4. The composition according to claim 1, wherein $M^2$ is Ti.

5. The composition according to claim 1, wherein $M^2$ is a metal oxide selected from the group consisting of Barium (Ba) oxide, titanium (Ti) oxide, Strontium (Sr) oxide, Tin (Sn) oxide, and Zirconium (Zr) oxide.

6. The composition according to claim 5, wherein $M^2$ is titanium (Ti) oxide.

7. The composition according to claim 1, wherein the compound of Formula I is selected from the group consisting of potassium titanium oxide oxalate, calcium titanium oxalate, potassium titanium oxide citrate, potassium calcium titanium oxalate and mixtures thereof.

8. The composition according to claim 7, wherein the compound of Formula I is potassium titanium oxide oxalate.

9. The composition according to claim 7, wherein the compound of Formula I is potassium titanium oxide citrate.

10. The composition according to claim 1, further comprising a pH buffer.

11. The compositions according to claim 10, wherein the pH buffer is a acid/acid salt combination selected from the group consisting of citric acid-sodium citrate, phosphoric acid-sodium phosphate, sodium monobasic phosphate, sodium dibasic phosphate, acetic acid-sodium acetate, succinic acid-sodium succinate, aconitic acid-sodium aconitate and benzoic acid-sodium benzoate.

12. The composition according to claim 1, wherein the ingredient is a flavorant.

13. The composition according to claim 1, wherein the ingredient is a sweetner.

14. The composition according to claim 1, wherein the composition is in the form of a mouthwash, mouthrinse, dentifrice, paste, powder, gel, tablet, lozenge, microcapsule, strip or strip coating.

15. The composition according to claim 1, wherein the composition is a coating or impregnant for dental devices selected from the group consisting of toothbrushes, toothbrush bristles, dental floss and dental pics.

16. The composition according to claim 1, further comprising an additional desensitizing agent, wherein the additional desensitizing agent is selected from the group consisting of potassium citrate, potassium chloride, potassium nitrate, citric acid, citric acid salts, strontium chloride, bioactive glass materials, phosphopeptides and mixtures thereof.

17. A method of treating sensitive teeth comprising the step of contacting the sensitive teeth with a composition according to claim 1 for at least about 10 seconds.

18. An oral composition comprising:
a) at least one compound of Formula I $$M^1\text{-}A\text{-}M^2\text{-}B\text{-}M^3 \qquad (I)$$

wherein: $M^1$ and $M^3$ are, independently, a monovalent or divalent metal selected from the group consisting of K and Li; $M^2$ is a polyvalent metal or metal oxide; and A and B are, independently, selected from the group consisting of $C_2$-$C_6$ diacids, triacids, and tetraacids;

b) water; and c) at least one or more of an ingredient selected from the group consisting of humectants, chelating agents, thickening agents, flavorants and preservatives, wherein the compound is dissolved in the water and is in an effective amount to induce tooth desensitization; and wherein the tooth sensitivity treatment composition has a pH of about 3.2 to about 4.5, provided that, if chelating agents are present, they are present at a level of from about 0.05% to about 0.25%.

* * * * *